United States Patent
Aoki

[11] Patent Number: 5,836,292
[45] Date of Patent: Nov. 17, 1998

[54] HEATER CONTROLLER FOR AN AIR-FUEL RATIO SENSOR

[75] Inventor: Keiichiro Aoki, Susono, Japan

[73] Assignee: Toyota Jidosha Kabushiki Kaisha, Aichi, Japan

[21] Appl. No.: 736,675

[22] Filed: Oct. 25, 1996

[30] Foreign Application Priority Data

Dec. 14, 1995 [JP] Japan .................................. 7-325977

[51] Int. Cl.⁶ .......................... F02D 41/00; F02M 23/00; F02M 25/00
[52] U.S. Cl. .......................................................... 123/697
[58] Field of Search ................................. 123/697, 489; 204/420, 406, 1 T, 424, 425

[56] References Cited

U.S. PATENT DOCUMENTS

| | | | |
|---|---|---|---|
| 4,694,809 | 9/1987 | Nakano et al. | 123/489 |
| 4,938,196 | 7/1990 | Hoshi et al. | 123/489 |
| 5,111,792 | 5/1992 | Nagai et al. | 123/697 |
| 5,148,795 | 9/1992 | Nagai et al. | 123/697 |
| 5,353,775 | 10/1994 | Yamashita et al. | 123/686 |

FOREIGN PATENT DOCUMENTS

| | | | |
|---|---|---|---|
| A-60-216255 | 10/1985 | Japan | 123/647 |
| A-60-21654 | 10/1985 | Japan | 123/647 |
| A-2-24550 | 1/1990 | Japan | 123/647 |

*Primary Examiner*—Raymond A. Neil
*Attorney, Agent, or Firm*—Oliff & Berribridge

[57] ABSTRACT

This invention provides a heater controller applied to an air-fuel ratio sensor to prevent the sensor being cooled after a return from a fuel-cut state.

The temperature of a detecting element 111 of an air-fuel ratio sensor 11 is maintained at a fixed temperature by beating the heater 112, and an electric power supplied to the heater is controlled by controlling a switching element 122 of a driving circuit 12 to a proper duty ratio. The sensor is cooled during the fuel-cut state because intake air is directly exhausted to an exhaust pipe, and the temperature of the sensor does not return to the proper temperature after a return from the fuel-cut state because the ambient temperature does not immediately return to the temperature before the fuel-cut state. Therefore a heater controller prevents the sensor being cooled by increasing an electric power after the return from the fuel-cut state in accordance with an integrated intake air-flow rate during the fuel-cut state.

20 Claims, 12 Drawing Sheets

Fig.6

| $Q_{afc}$ \ $Q_{fc}$ | 400 | 200 |
|---|---|---|
| 20 | 10 | 5 |
| 50 | 8 | 4 |
| 80 | 6 | 2 |
| 120 | 4 | 0 |
| 150 | 2 | 0 |
| 180 | 0 | 0 |

Fig.10

| $Q_{afc}$ \ $\Delta T$ | 15 | 8 |
|---|---|---|
| 20 | 10 | 5 |
| 50 | 8 | 4 |
| 80 | 6 | 2 |
| 120 | 4 | 0 |
| 150 | 2 | 0 |
| 180 | 0 | 0 |

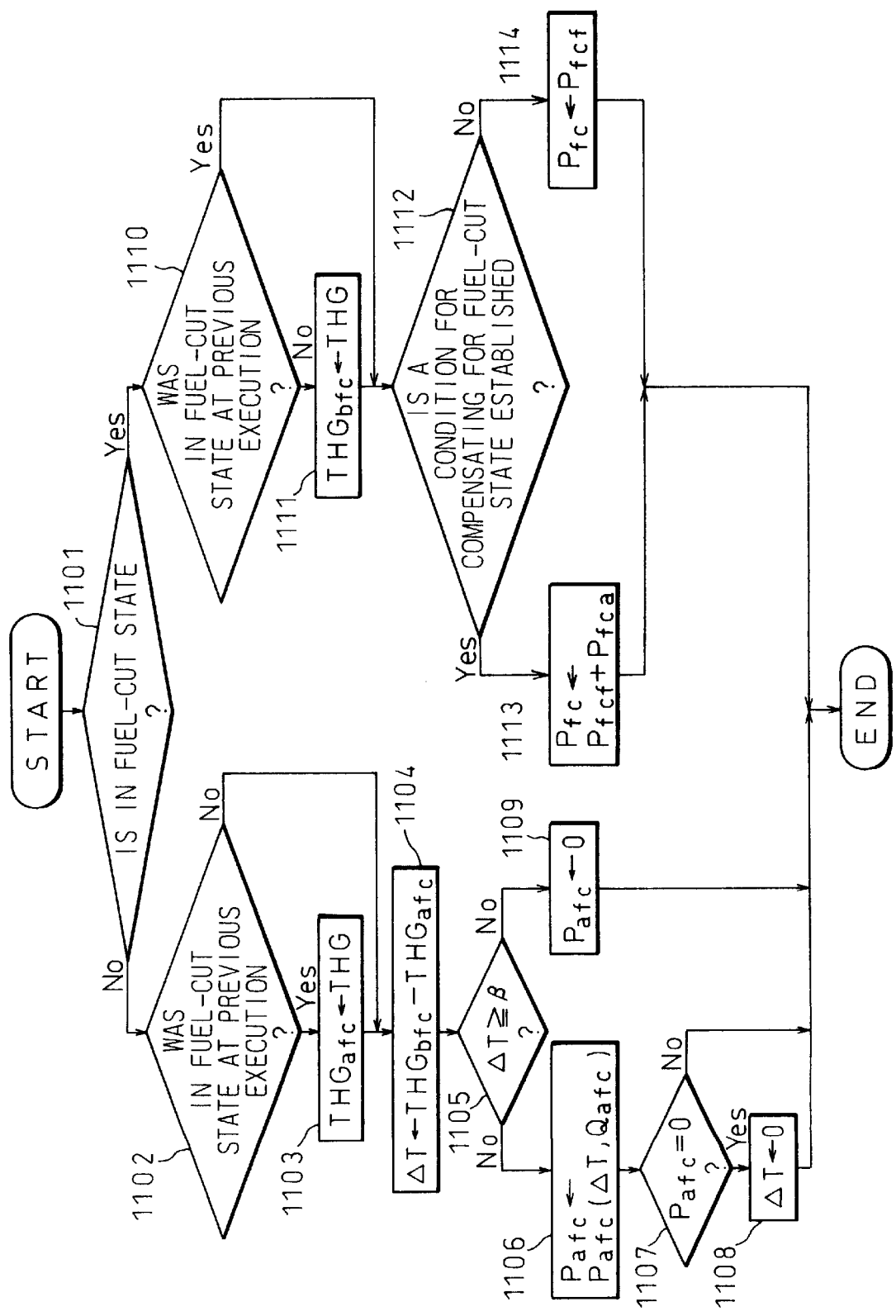

HEATER CONTROLLER FOR AN AIR-FUEL RATIO SENSOR

BACKGROUND OF THE INVENTION

1. Field of the Invention

This invention relates to a heater controller for an air-fuel ratio sensor, and especially relates to a heater controller for controlling electric power supplied to a heater for heating the air-fuel ratio sensor to prevent the sensor being cooled by a low-temperature atmosphere around the sensor after a return from a fuel-cut state.

2. Description of the Related Art

It is widely known to control an air-fuel ratio of air-fuel mixture supplied into a cylinder of an engine at a fixed target air-fuel ratio (for example, the stoichiometric air-fuel ratio) by correcting a basic fuel flow rate in accordance with oxygen contained in exhaust gas in order to improve the exhaust gas emission, the specific fuel consumption and the vehicle drivability.

To achieve the above-mentioned air-fuel ratio control, it is indispensable to detect the oxygen contained in the exhaust gas. It is also necessary to keep the temperature of an air-fuel ratio sensor at a fixed temperature (for example, 650° C.) by heating the sensor with a heater, because the output voltage of the sensor is influenced not only by the oxygen concentration but also by the temperature of the sensor.

However, as the temperature of the sensor is influenced by the temperature of the exhaust gas, a heater controller which controls a basic electric power supplied to the heater according to the operating condition of the engine which influences the temperature of exhaust gas has been proposed.

Further, a heater controller which adds an auxiliary electric power to the basic electric power during a fuel-cut state to prevent the air-fuel ratio sensor being cooled, has been also proposed (See Japanese Unexamined Patent Publication 60-216254 and Japanese Unexamined Patent Publication 60-216255).

According to the above-mentioned heater controller, however, the auxiliary electric power is immediately cancelled at a return from the fuel-cut state, and only the basic electric power is supplied to the heater after the return from the fuel-cut state. Therefore, it is unavoidable that the sensor is cooled after the return from the fuel-cutting state, because an atmosphere around the sensor does not quickly return to the temperature before the fuel-cut state, after the return of the fuel-cut condition.

SUMMARY OF THE INVENTION

Accordingly, an object of this invention is to provide a heater controller for air-fuel ratio sensor able to prevent the sensor being cooled by a low temperature atmosphere around the sensor after a return from a fuel-cut state.

According to an aspect of this invention, there is provided a heater controller, for controlling an electric power supplied to a heater for heating an air-fuel ratio sensor which detects an air-fuel ratio of an internal combustion engine, comprising an engine condition detecting means for detecting an operating condition of the engine; a basic electric power determining means for determining a basic electric power supplied to the heater in accordance with the engine operating condition detected by said engine condition detecting means; a fuel-cut state detecting means for detecting whether or not the engine is operating under a fuel-cut state; an index calculating means for calculating an index which denotes a temperature fall in an atmosphere around the sensor when it is determined that the engine is operating under the fuel-cut state by said fuel-cut state determining means; an auxiliary electric power determining means for determining an auxiliary electric power in accordance with the index calculated by said index calculating means when it is determined that the engine has returned from the fuel-cut state by said fuel-cut state detecting means; and an electric power supply means for supplying an electric power which is a sum of the basic electric power determined by said basic electric power determining means and the auxiliary electric power determined by said auxiliary electric power determining means.

The heater controller according to the present invention can prevent the temperature of the air-fuel ratio sensor decreasing after a return from a fuel-cut state, because the electric power supplied to the heater for heating the sensor is increased after the return from the fuel-cut state in accordance with the index which denotes a temperature fall in an atmosphere around the sensor during the fuel-cut state.

BRIEF DESCRIPTION OF THE DRAWINGS

The present invention will be more clearly understood from the description set forth below with reference to the accompanying drawings; where.

FIG. 6 is a map to determine an auxiliary electric power after a return from a fuel-cut state;

FIG. 10 is a second map to determine an auxiliary electric power after a return from a fuel-cut state;

FIG. 11 is a flow chart of a third fuel-cut routine; and

DETAILED DESCRIPTION OF THE PREFERRED EMBODIMENT

Figure 1:
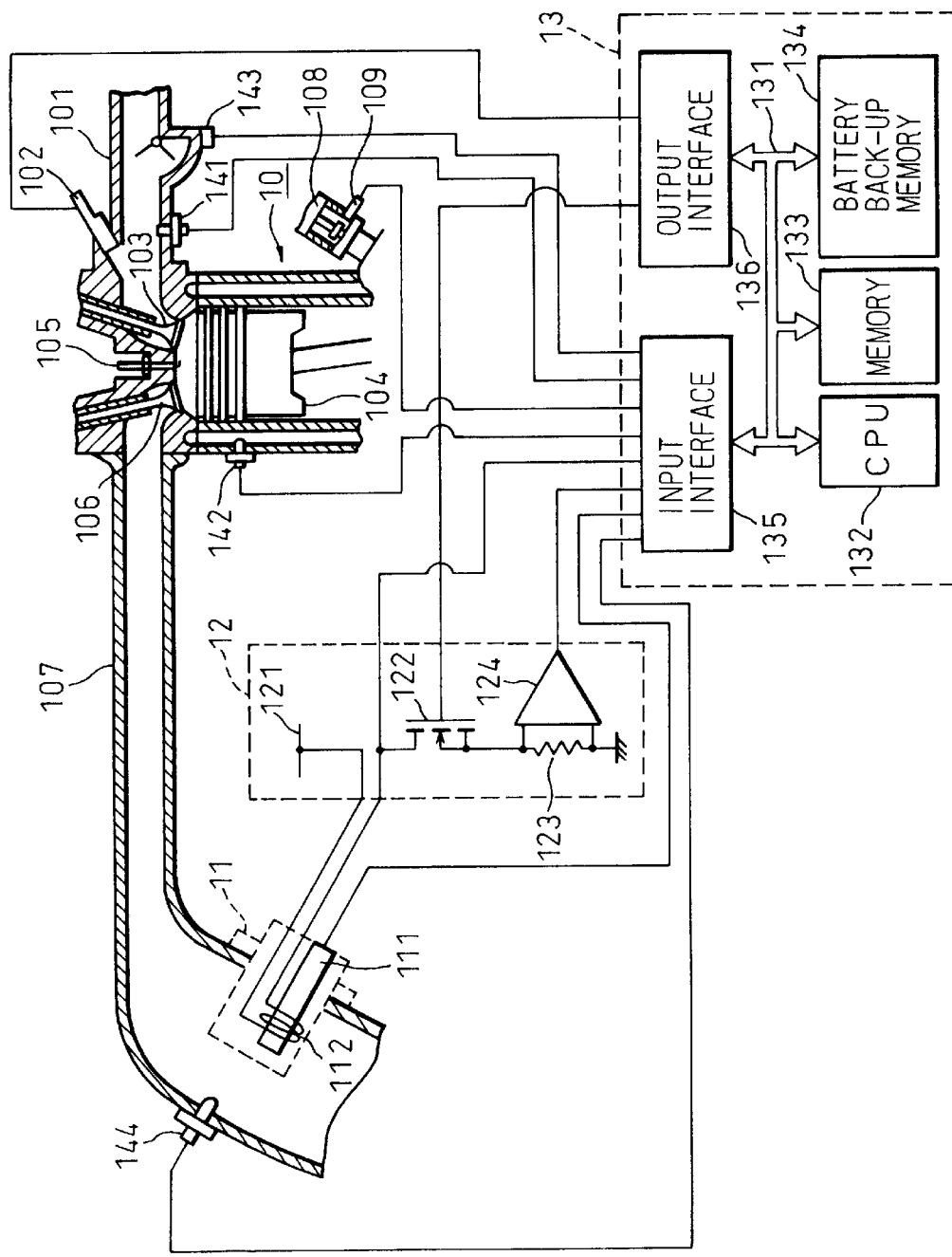
FIG. 1 is a block diagram of a preferred embodiment of a heater controller according to this invention.

FIG. 1 shows a diagram of the preferred embodiment of a heater controller for an air-fuel ratio sensor according to the present invention, wherein a mixture composed of air supplied through an intake pipe 101 and fuel injected from an injector 102 is supplied to an internal combustion engine 10 through an intake valve 103.

The mixture is compressed by a piston 104, and the compressed mixture is ignited by an igniter 105 and then pushes down the piston 104. Exhaust gas produced by the burning of the mixture is exhausted to an exhaust pipe 107 through an exhaust valve 106.

The engine speed of the engine 10 is detected by a speed detector 109 built into a distributor 108.

On the exhaust pipe 107, an air-fuel ratio sensor 11 is installed. The air-fuel ratio sensor 11 has a detecting element 111 which detects oxygen density and a heater 112 which beats the detecting element 111.

The heater obtains electric power from a driving circuit 12 which is composed of an electric power source 121, a switching element 122, a resistor 123 for measuring current, and a buffer amplifier 124.

The heater 112, the switching element 122, and the resistor 123 are connected in series between the electric power source 121 and a ground (the vehicle body). A current flowing through this series connection is detected by measuring a voltage across the resistor 123 for measuring current using the buffer amplifier 124.

A controller 13 is a microcomputer system which is composed of a bus 131, a CPU 132, a memory 133, a battery-backup memory 134, an input interface 135, and an output interface 136. Note, data stored in the battery-backup memory 134 is not lost when a main switch of the automobile is turned off and further an ignition key is drawn, as long as the battery-backup memory 134 is not removed from a battery (that is, as long as the memory is not cleared by removing the backup battery).

Not only the speed detector 109 and the detecting element 111 of the air-fuel ratio sensor 11, but also a vacuum sensor 141 installed on the intake pipe 101, a coolant temperature sensor 142, an air flow meter 143 and an exhaust gas temperature sensor 144 are connected to the input interface 135.

A valve opening command for the injector 102 and an ON/OFF command for the switching element 122 are output from the output interface 136.

Figure 2:
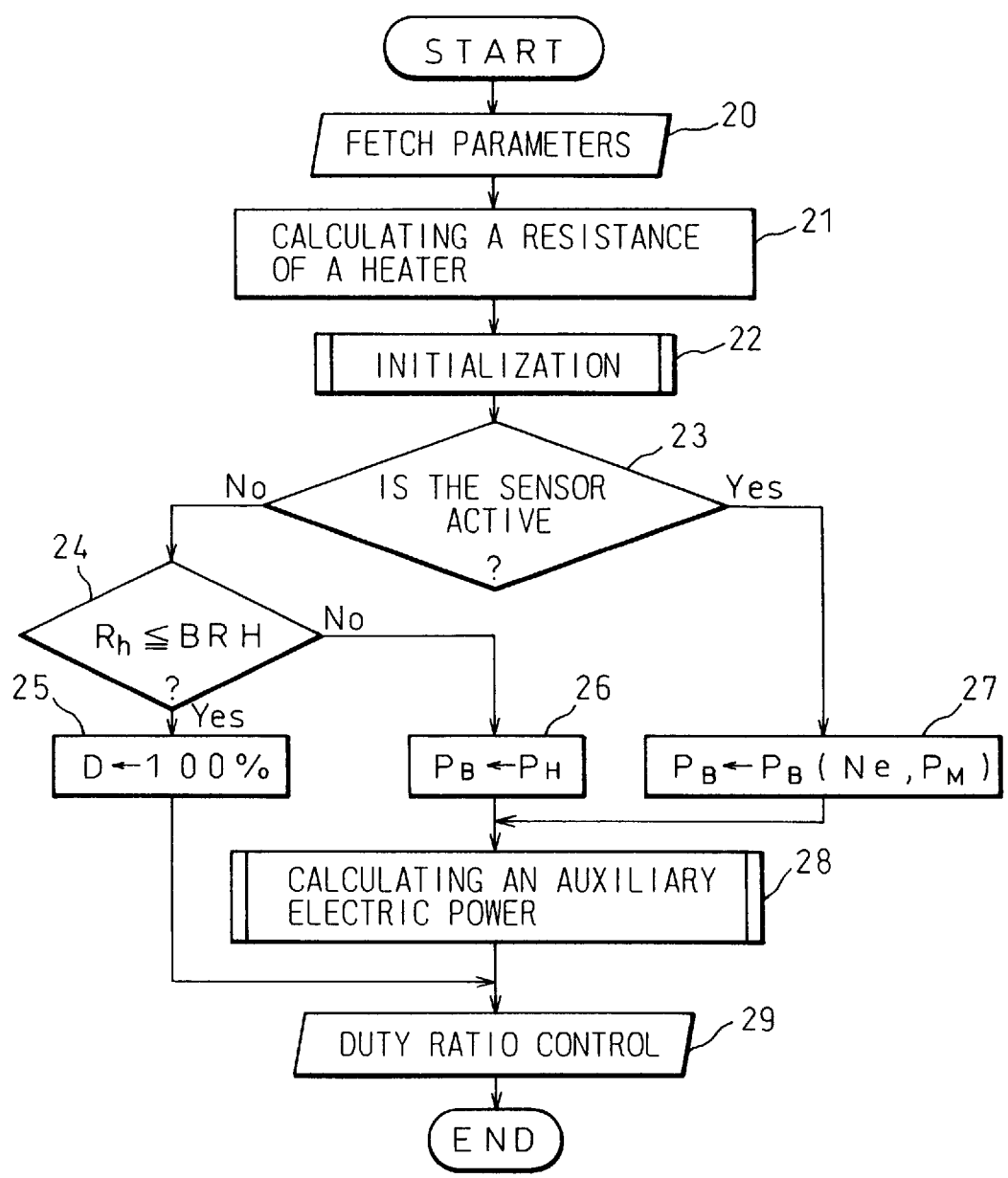
FIG. 2 is a flow chart of a heater control routine.

FIG. 2 is a flow chart of the heater control routine executed in the controller 13. An engine speed Ne, an intake vacuum Pm, a voltage Vh at the connecting point of the heater 112 and the switching element 122, a current Ih flowing through the heater and an intake air flow Qa are fetched at step 20.

At step 21, a resistance Rh of the heater is calculated in accordance with a battery voltage Vb, the voltage Vh at the connecting point of the heater and the switching element and the current Ih flowing through the heater using a following equation.

$$Rh \leftarrow (Vb-Vh)/Ih$$

After the initializing routine is executed at step 22, it is determined whether or not the air-fuel ratio sensor is active at step 23. An activation of the sensor 11 may be determined by determining whether or not an output of the sensor exceeds a predetermined level.

When the determination at step 23 is negative, that is, when the sensor 11 is not active, the control proceeds to step 24 where it is determined whether or not the resistance of the heater calculated at step 21 is smaller than a predetermined upper limit resistance (for example, a stored resistance BRH).

When the determination at step 24 is affirmative, that is, when the resistance Rh of the heater is smaller than BRH, the control proceeds to step 29 after a duty ratio D is set to 100% in order to accelerate an activation of the sensor at step 25.

When the determination at step 24 is negative, that is, when the resistance Rh of the heater is larger than BRH, the control proceeds to step 28 after a basic electric power is set to a predetermined electric power Ph required to maintain the temperature of a standard heater at 1100° C. at step 26.

When the determination at step 23 is affirmative, that is, when the sensor is active, the control proceeds to step 28 after a basic electric power Pb is calculated as a function of the engine speed Ne and the intake vacuum Pm at step 27.

$$Pb \leftarrow Pb(Ne, Pm)$$

After the basic electric power Pb is calculated at step 26 or step 27, the control proceeds to step 28 where the auxiliary electric power calculating routine is executed. Then this routine is terminated after a switching element 122 is controlled at step 29 with the duty ratio determined at step 25 or step 28.

Figure 3:
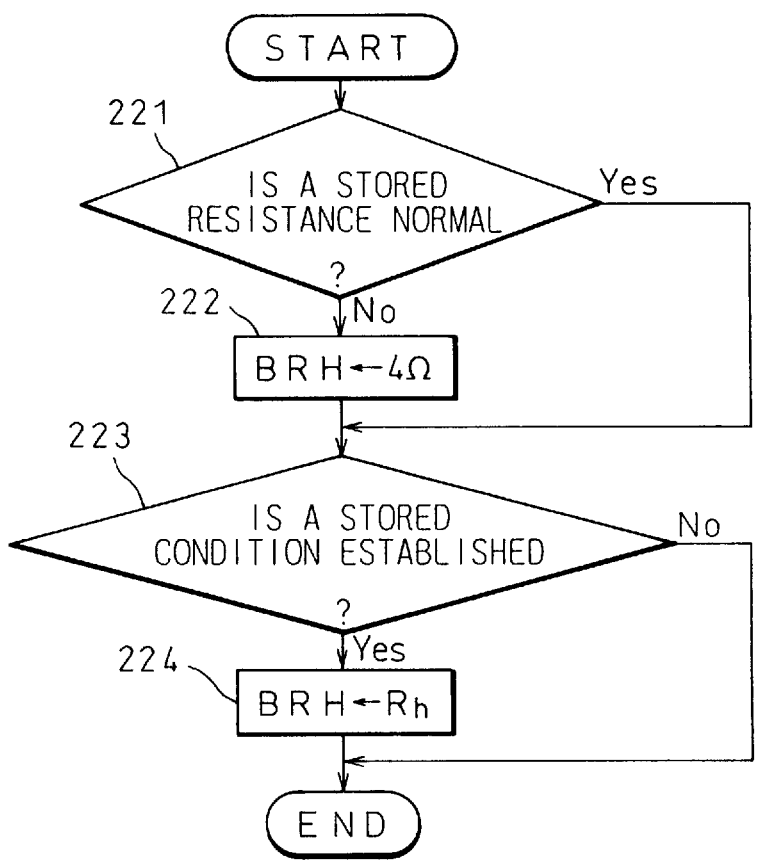
FIG. 3 is a flow chart of an initializing routine.

FIG. 3 shows a flow chart of the initializing routine executed at step 22 of the heater control routine, and it is determined whether or not a stored resistance of the heater stored in the battery backup memory 134 is normal at step 221.

The above-mentioned determination, for example, can be realized by storing not only the resistance of the heater but also its reciprocal at a storing stage and confirming that those two numbers are mutually in a reciprocal relationship when determining whether or not the stored resistance is normal.

When the determination at step 221 is negative, the control proceeds to step 223 after the stored resistance BRH is set to the predetermined standard value (for example, 4 ohms) at step 222. Note, when the determination at step 221 is affirmative, the control proceeds directly to step 223.

At step 223, it is determined whether or not a condition for storing of the resistance of the heater is established.

The storing condition is established when the temperature of the heater is controlled at a constant temperature and the operating condition of the automobile is stable. This condition can be confirmed by determining whether or not following three conditions are established.

(1) Whether or not an air-fuel ratio feedback control is being executed.
(2) Whether or not the state that the intake pressure Pm is below a predetermined fixed pressure and the engine speed Ne is below a predetermined fixed speed continues for a fixed predetermined interval.
(3) Whether or not the electric power supplied to the heater is above a predetermined fixed power.

When the determination at step 223 is affirmative, that is, when the storing condition is established, this routine is terminated after the stored resistance BRH is replaced with Rh which is calculated at step 21 of the heater control routine at step 224.

Note, when the determination at step 233 is negative, this routine is directly terminated without replacing of the stored resistance BRH.

Figure 4:
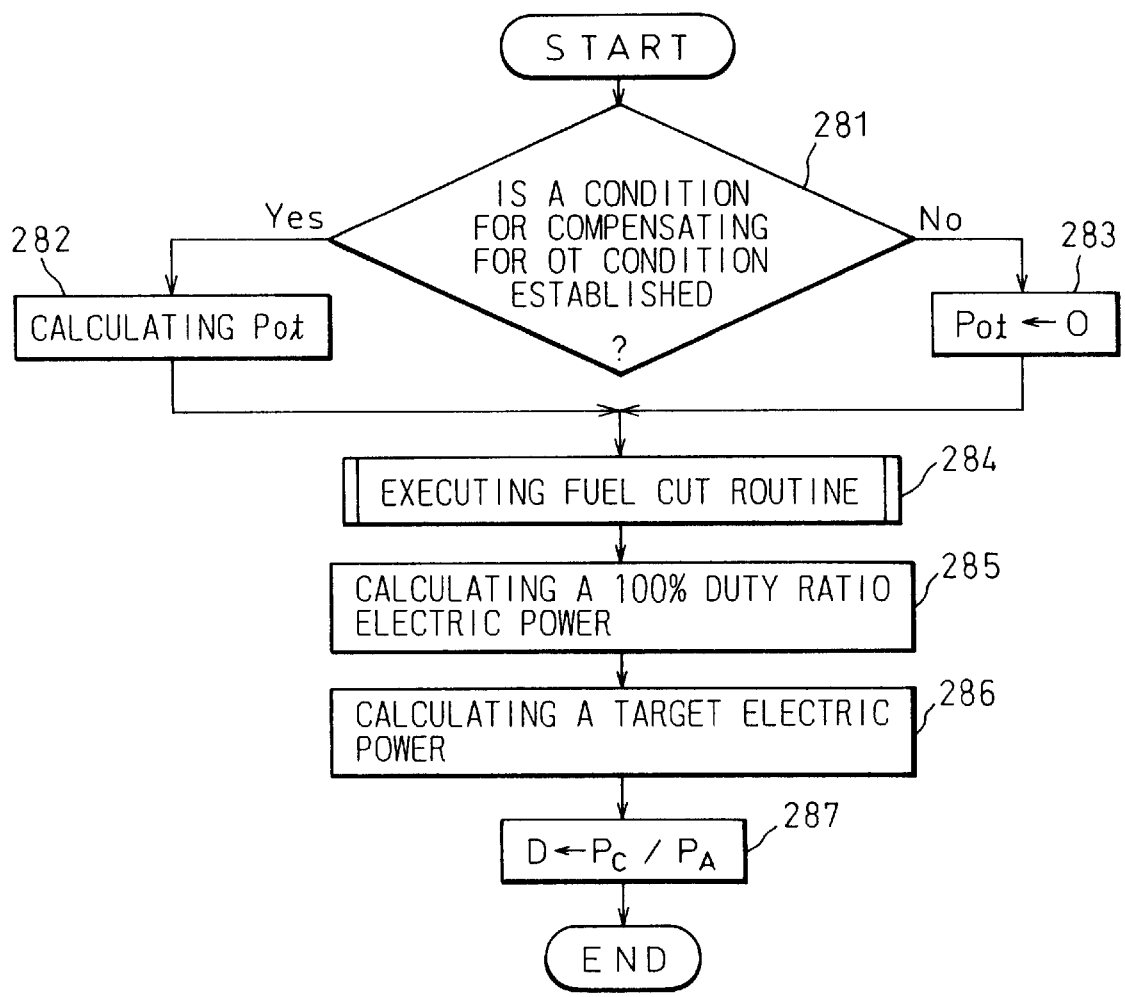
FIG. 4 is a flow chart of an auxiliary electric power determining routine.

FIG. 4 is a flow chart of an auxiliary electric power determining routine, executed at step 28 of the heater control routine, which determines whether or not a condition for compensating for an over temperature state (hereafter, OT condition) is established. This is because an increase in an electric power becomes meaningless as the electric power is decreased when the OT condition is established.

When the determination at step 281 is affirmative, the control proceeds to step 284 after an auxiliary electric power Pot for compensating for an over temperature state is determined at step 282.

When the determination at step 281 is negative, the control proceeds to step 284 after an auxiliary electric power Pot for compensating for an over temperature state is set to "0" at step 283.

At step 284, the fuel-cut routine is executed.

At step 285, an electric power Pa continuously supplied to the heater for a predetermined fixed period (for example, 100 ms), that is, an electric power at 100% duty ratio is calculated based on the voltage Vh at the connecting point of the heater and the switching element and the current Ih flowing through the heater fetched at step 20.

At step 286, a target electric power Pc is calculated by adding all auxiliary electric powers to the basic electric power Pb.

$$Pc \leftarrow Pb+Pot+Pfc+Pafc$$

This routine is terminated after a duty ratio D is calculated as a ratio of the target electric power Pc to the electric power Pa at 100% duty ratio at step 287.

$$D \leftarrow Pc/Pa$$

Figure 5:
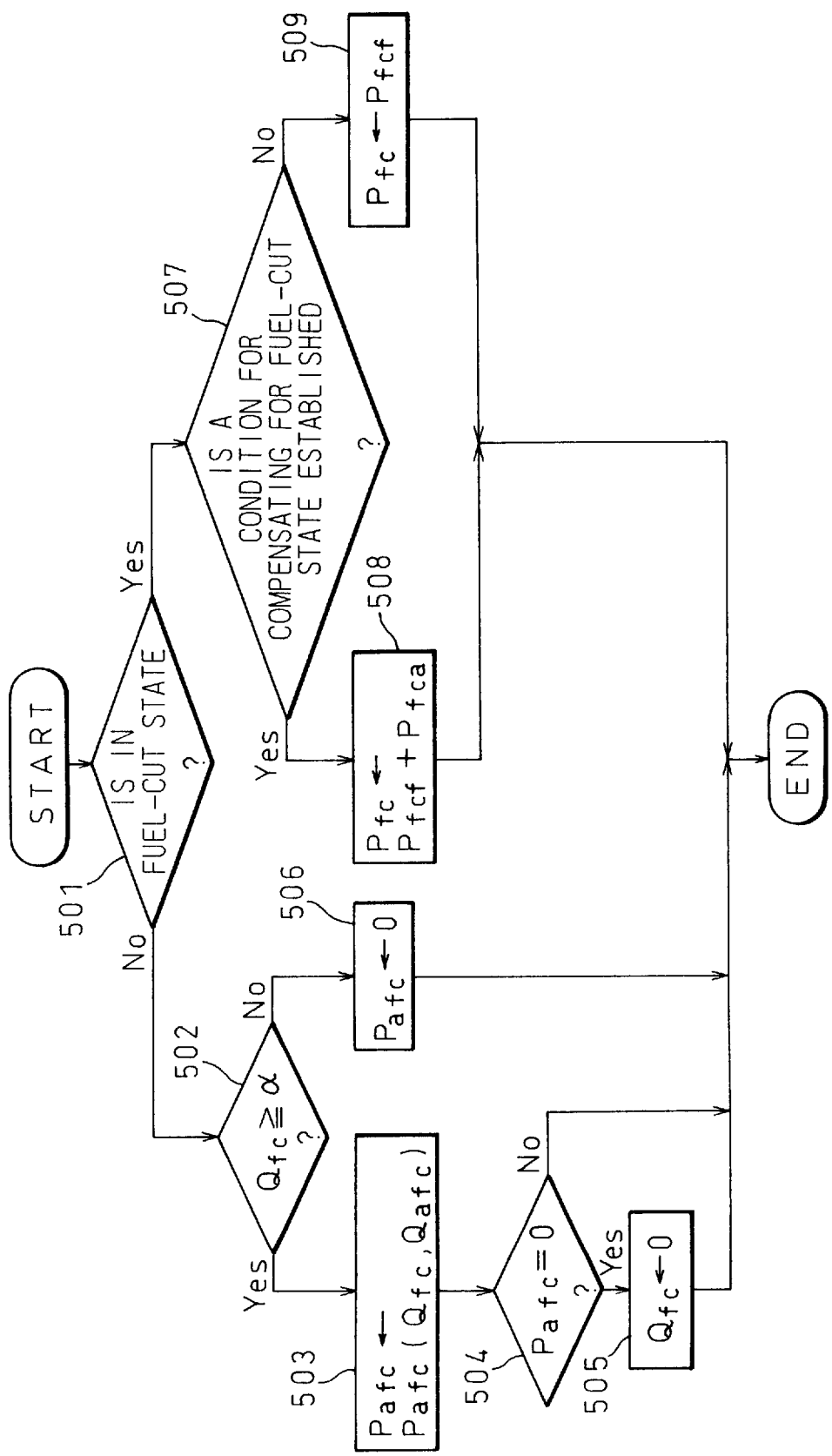
FIG. 5 is a flow chart of a first fuel-cut routine.

FIG. 5 is a flow chart of a first fuel-cut routine, executed at 284 of the auxiliary electric power determining routine, which determines whether or not the engine is operating under a fuel-cut state at step 501.

When the determination at step 501 is negative, that is, when the engine returns from the fuel-cutting state, the control proceeds to step 502 where it is determined whether or not an integrated air flow rate Qfc during the fuel-cut state is larger than the predetermined fixed value a.

When the determination at step 502 is affirmative, that is, when the sensor has been cooled by the low-temperature atmosphere around the sensor because the intake air has been directly exhausted during the fuel-cut state, the control proceeds to step 503 where an auxiliary electric power Pafc for compensating for a return of the fuel-cut state is calculated as a function of the integrated air-flow rate Qfc during the fuel-cut state and an integrated air-flow rate Qafc after a return from the fuel-cut state.

$$Pafc \leftarrow Pafc\ (Qfc,\ Qafc)$$

Note, the auxiliary electric power Pafc for compensating for the return of the fuel-cut state is influenced not only by the integrated air-flow rate Qfc during the fuel-cut state but also by the integrated air-flow rate Qafc after the return from the fuel-cut state, because the sensor is cooled not only by the air flow during the fuel-cutting state but also by low-temperature exhaust gas after the return from the fuel-cut state.

FIG. 6 is a first map to determine the auxiliary electric power Pafc for compensating for the return of the fuel-cut state, and this map is stored in the memory 133. Its row denotes an integrated air-flow rate Qfc during a fuel-cut state and its column denotes an integrated air-flow rate Qafc after a return of a fuel-cut state.

The larger the integrated air-flow rate Qfc is, the larger the auxiliary electric power Pafc becomes, and the larger the integrated air-flow Qafc is, the smaller the auxiliary electric power Pafc becomes.

It is determined whether or not the auxiliary electric power Pafc is "0.0" at step 504. When its determination is affirmative, this routine is terminated after resetting the integrated air-flow rate Qfc to "0.0" as the auxiliary electric power Pafc for compensating for a return of a fuel-cut state is no longer necessary.

When the determination at step 504 is negative, the routine is directly terminated.

When the determination at step 502 is negative, this routine is terminated after the auxiliary electric power Pafc is set to "0.0" at step 506 because an atmosphere around the sensor 11 is not cooled as an interval of a fuel-cut state is short.

When the determination at step 501 is affirmative, that is, when the engine is operating under a fuel-cut state, the control proceeds to step 507 where it is determined whether or not a condition for compensating for a temperature fall in the exhaust during the fuel-cut state is established.

When the determination at step 507 is affirmative, this routine is terminated after calculating the auxiliary electric power Pfc during the fuel-cut state as a sum of a fundamental electric power during fuel-cutting state Pfcf and an additional electric power during fuel-cut state Pfca.

When the determination at step 507 is negative, this routine is terminated after setting the auxiliary electric power Pfc to the fundamental electric power Pfcf.

Figure 7:
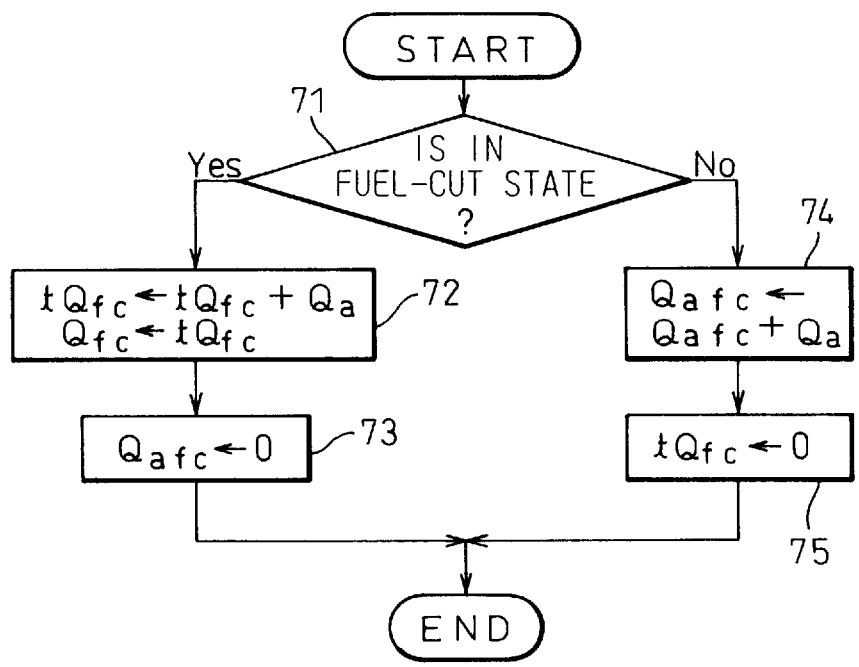
FIG. 7 is a flow chart of a first air-flow rate integrating routine.

FIG. 7 is a flow chart of a first air-flow rate integrating routine independently executed from above-explained routines, which determines whether or not the engine is operating under a fuel-cut state.

When the determination at step 71 is affirmative, that is, when the engine is operating under the fuel-cut state, the control proceeds to step 72 where a temporary integrated air-flow rate tQfc during the fuel-cut state is renewed by adding the current air-flow rate Qa to the previous temporary integrated air-flow rate tQfc and an integrated air-flow rate Qfc is set to the temporary integrated air-flow rate tQfc. The control is terminated after setting the integrated air flow Qafc after a return from a fuel-cut state to "0.0" at step 73.

When the determination at step 71 is negative, that. is, when the engine is not operating under a fuel-cut state, the control proceeds to step 74 where the integrated air flow Qafc after a return from a fuel-cut state is renewed by adding the current air flow Qa to the previous integrated air flow Qafc. The control is terminated after setting the temporary integrated air flow tQfc during a fuel-cut state to "0.0" at step 75.

Though it is possible to prevent the air-fuel ratio sensor 11 being cooled after a return from a fuel-cut state according to the first air flow integrating routine, it is not possible to prevent the sensor being cooled when the engine is operated frequently in a fuel-cut state with a short interval because the auxiliary electric power Pafc after a return from a fuel-cut state becomes small as the integrated air-flow rate Qfc during a fuel-cut state is small.

Figure 8:
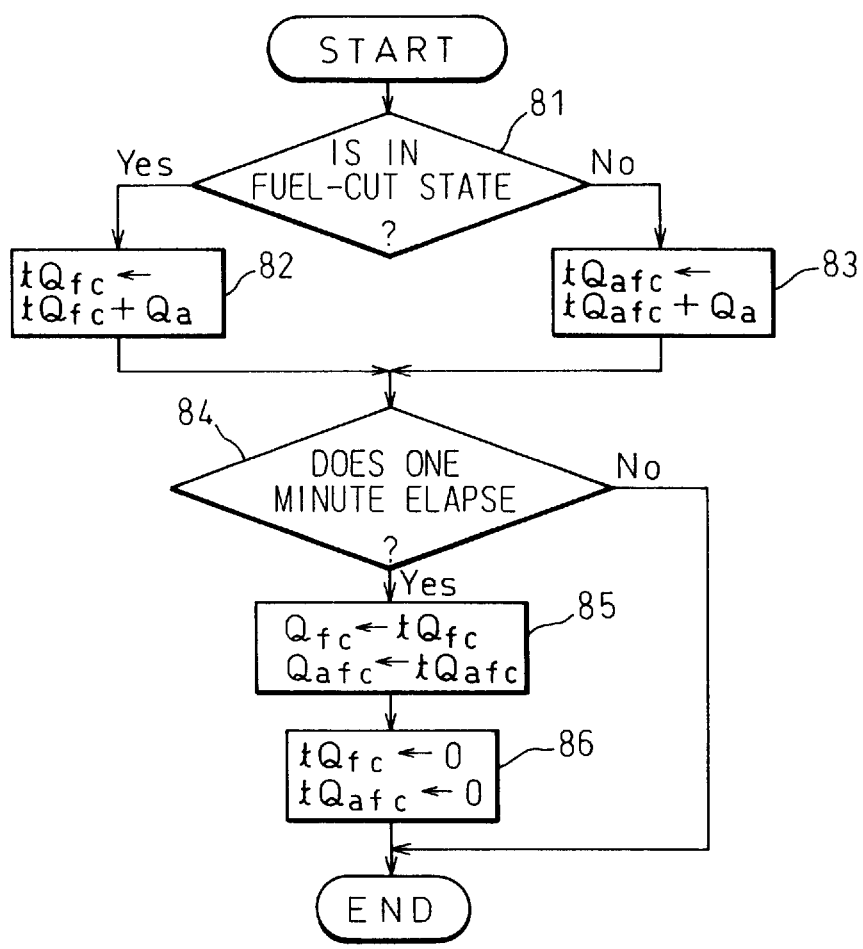
FIG. 8 is a flow chart of a second air-flow rate integrating routine.

A second air-flow integrating routine, shown in FIG. 8 is used to solve the above-mentioned problem, and an integrated air-flow rate is renewed every predetermined interval in the fuel-cut routine.

It is determined whether or not the engine is operating under a fuel-cut state at step 81. When the determination at step 81 is affirmative, that is, when the engine is operating under the fuel-cut state, the control proceeds to step 84 after a temporary integrated air flow tQfc during the fuel-cut state is renewed by adding the current air flow Qa to the previous temporary integrated air-flow rate tQfc at step 82.

When the determination at step 81 is negative, that is, when the engine is not operating under the fuel-cut state, the control proceeds to step 84 after the temporary integrated air flow tQafc after a return from a fuel-cut state is renewed by adding the current air-flow rate Qa to the Previous temporary integrated air-flow rate tQafc at step 83.

It is determined whether or not a predetermined fixed period (for example, one minute) has elapsed at step 84. When the determination at step 84 is affirmative, the control proceeds to step 85 where the integrated air-flow rate Qfc during a fuel-cut state and the integrated air-flow rate Qafc after a return from the fuel-cut state which are used in the fuel-cut routine of FIG. 5, are renewed by replacing Qfc with tQfc and Qafc with tQafc.

Then this routine is terminated after the temporary integrated air-flow rate tQfc during a fuel-cut-state and the temporary integrated air-flow rate tQafc after a return from a fuel-cut state are reset at step 86.

Note, when the determination at step 84 is negative, this routine is directly terminated.

The integrated air-flow rate during a fuel-cut state is used as the index which denotes a temperature fall in an atmosphere around the air-fuel ratio sensor 11 in the first fuel-cut routine, a temperature fall in the coolant during a fuel-cut state or a temperature fall in the exhaust gas during a fuel-cut state may be used instead of the integrated air-flow rate.

Figure 9:
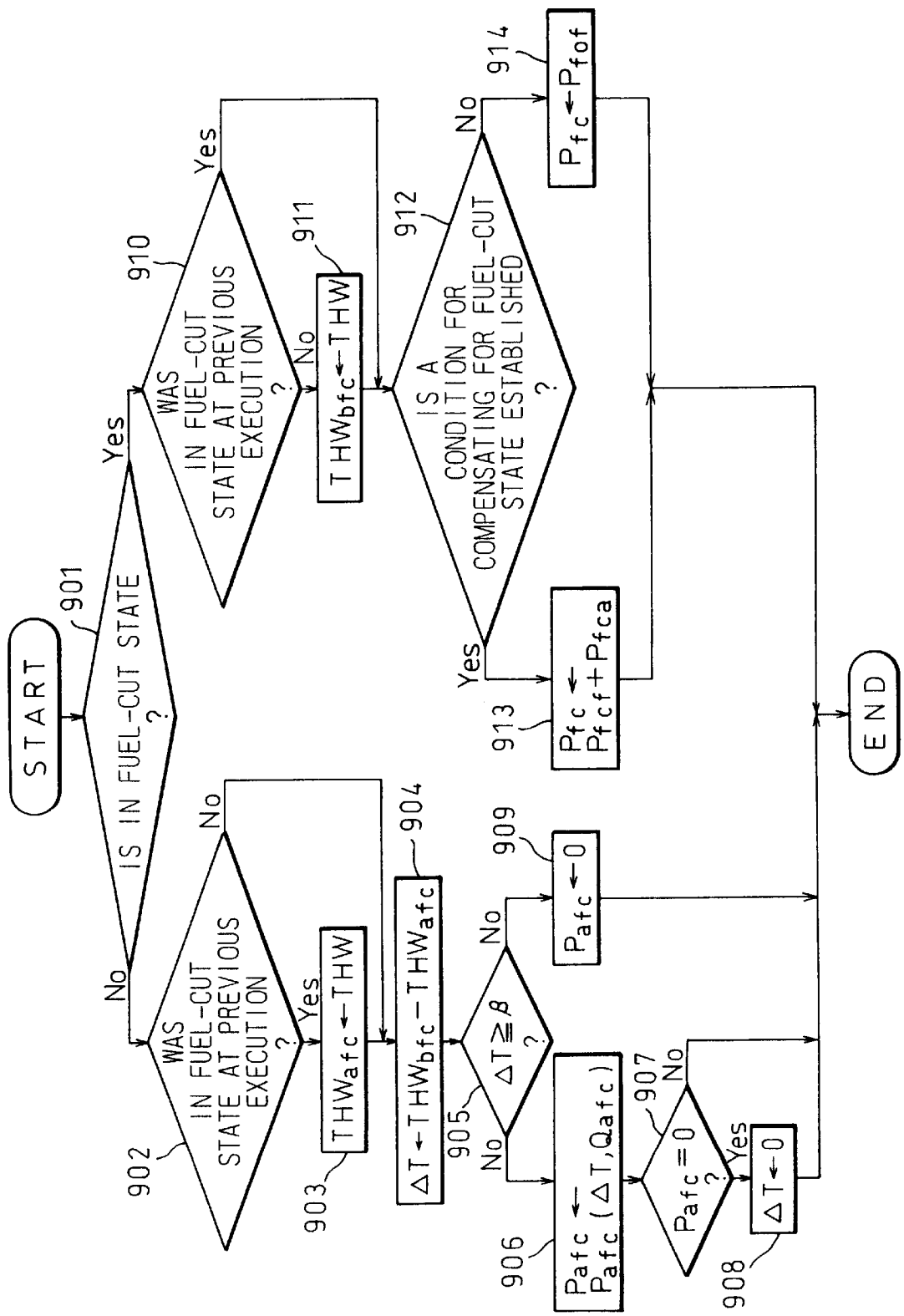
FIG. 9 is a flow chart of a second fuel-cut routine.

FIG. 9 is a flow chart of a second fuel-cut routine, and a temperature fall in the coolant during a fuel-cut state is used as an index which denotes a temperature fall in an atmosphere around the air-fuel ratio sensor 11. Note, the coolant temperature is fetched at step 20 of the heater control routine in this case.

It is determined whether or not the engine is operating under a fuel-cut state at step 901. When its determination is negative, it is determined whether or not the engine was operating under a fuel-cut state at the previous execution at step 902.

When the determination at step 902 is affirmative, the control proceeds to step 904 after a current coolant temperature THW is set as a coolant temperature THWafc after the return from the fuel-cut state at step 903. Note, when the determination at step 902 is negative, the control proceeds directly to step 904.

A temperature difference $\Delta T$ between a coolant temperature THWbfc before the fuel-cut state and a coolant temperature THWafc after the return from the fuel-cut state is calculated at step 904, and the control proceeds to step 905.

$$\Delta T \leftarrow THWbfc - ThWafc$$

It is determined whether or not the temperature difference is larger than a predetermined temperature difference $\beta$.

When the determination at step 905 is affirmative, the control proceeds to step 906 where an auxiliary electric power Pafc after the return from the fuel-cut state is calculated as a function of the temperature difference $\Delta T$ and the integrated air flow rate Qafc after the return from the fuel-cut state.

$$Pafc \leftarrow Pafc\ (\Delta T, Qafc)$$

FIG. 10 shows the second map to determine the auxiliary electric power Pafc after the return from the fuel-cut state, and this map is stored in the memory 133. Its row denotes the temperature difference $\Delta T$ and its column denotes the integrated air-flow rate Qafc after a return from the fuel-cut state.

The larger the temperature difference $\Delta T$ becomes, the larger the auxiliary electric power Pafc after a return from a fuel-cut state becomes, and the larger the integrated air flow rate Qafc becomes, the smaller the auxiliary electric power Pafc becomes.

At step 907, it is determined whether or not the auxiliary electric power Pafc after a return from a fuel-cut state is "0.0". When the determination at step 907 is affirmative, this routine is terminated after the temperature difference $\Delta T$ is set to "0.0" to maintain the auxiliary electric power Pafc at "0.0" thereafter at step 908. Note, when the determination at step 907 is negative, the control is directly terminated.

When the determination at step 905 is affirmative, this routine is terminated after the auxiliary electric power Pafc is set to "0.0" at step 909 because the compensation is not necessary as the temperature fall in the atmosphere around the sensor is small.

When the determination at step 901 is affirmative, that is, when the engine is operating under a fuel-cut state, the control proceeds to step 910 where it is determined whether or not the engine was operating under the fuel-cut state at the previous execution.

When the determination at step 910 is negative, that is, when the engine was not operating under the fuel-cut state, the control proceeds to step 912 after a coolant temperature THWbfc before the fuel-cut state is set to a current coolant temperature THW at step 911. Note, when the determination at step 910 is negative, the control proceeds directly to step 912.

At step 912, it is determined whether or not a condition for compensating for a temperature fall in the atmosphere during the fuel-cut state is established.

When the determination at step 912 is affirmative, this routine is terminated after calculating the auxiliary electric power Pfc during the fuel-cut state as a sum of a fundamental electric power during fuel-cutting state Pfcf and an additional electric power during fuel-cut state Pfca.

When the determination at step 912 is negative, this routine is terminated after setting the auxiliary electric power Pfc to the fundamental electric power Pfcf.

Note, the integrated air-flow rate Qafc after the return from the fuel-cut state is calculated in the first or second air-flow integrating routine.

FIG. 11 is a flow chart of a third fuel-cut routine, and a temperature fall in the exhaust gas during fuel-cut state is used as the index which denotes the temperature fall in the atmosphere around the sensor 11. Note, the exhaust gas temperature THG is also fetched at step 20 of the heater control routine in this case.

It is determined whether or not the engine is operating under a fuel-cut state at step 1101. When its determination is negative, it is determined whether or not the engine was operating under a fuel-cut state at the previous execution at step 1102.

When the determination at step 1102 is affirmative, the control proceeds to step 1104 after an exhaust gas temperature THGafc after the return from the fuel-cut state is set to a current exhaust gas temperature THG at step 1103. Note, when the determination at step 1102 is negative, the control proceeds directly to step 1104.

After a temperature difference $\Delta T$ between an exhaust gas temperature THGbfc before the fuel-cut state and an exhaust gas temperature THGafc after the return form the fuel-cut state is calculated at step 1104, the control proceeds to step 1105.

$$\Delta T \leftarrow THGbfc - THGafc$$

It is determined whether or not the temperature difference is larger than a predetermined temperature difference $\beta$ at step 1105.

When the determination at step 1105 is affirmative, the control proceeds to step 1106 where an auxiliary electric power Pafc after the return from the fuel-cut state is calculated as a function of the temperature difference $\Delta T$ and the integrated air flow rate Qafc after the return from the fuel-cut state.

$$Pafc \leftarrow Pafc\ (\Delta T, Qafc)$$

The auxiliary electric power Pafc after the return from the fuel-cut state can be determined using the same map as the second map.

At step 1107, it is determined whether or not the auxiliary electric power Pafc after a return from a fuel-cut state is "0.0". When its determination is affirmative, this routine is terminated after the temperature difference $\Delta T$ is set to "0.0" to maintain the auxiliary electric power Pafc at "0.0" thereafter at step 1108. Note, when the determination at step 1107 is negative, the control is directly terminated.

When the determination at step 1105 is affirmative, this routine is terminated after the auxiliary electric power Pafc is set to "0.0" at step 1109 because the compensation is not necessary as the temperature descent of the atmosphere around the sensor is small.

When the determination at step 1101 is affirmative, that is, when the engine is operating under a fuel-cut state, the control proceeds to step 1110 where it is determined whether or not the engine was operating under the fuel-cut state at the previous execution.

When the determination at step 1110 is negative, that is, when the engine was not operating under the fuel-cut state, the control proceeds to step 1112 after an exhaust gas temperature THGbfc before the fuel-cut state is set to a current exhaust gas temperature THG at step 1111. Note, when the determination at step 1110 is negative, the control proceeds directly to step 1112.

At step 1112, it is determined whether or not a condition for compensating for a temperature fall in the atmosphere during the fuel-cut state is established.

When the determination at step 1112 is affirmative, this routine is terminated after calculating the auxiliary electric power Pfc during the fuel-cut state as a sum of a fundamental electric power during the fuel-cutting state Pfcf and an additional electric power during the fuel-cut state Pfca.

When the determination at step 1112 is negative, this routine is terminated after setting the auxiliary electric power Pfc to the fundamental electric power Pfcf.

Note, the integrated air-flow rate Qafc after the return from the fuel-cut state is calculated in the first or second air-flow integrating routine.

Figure 12A:
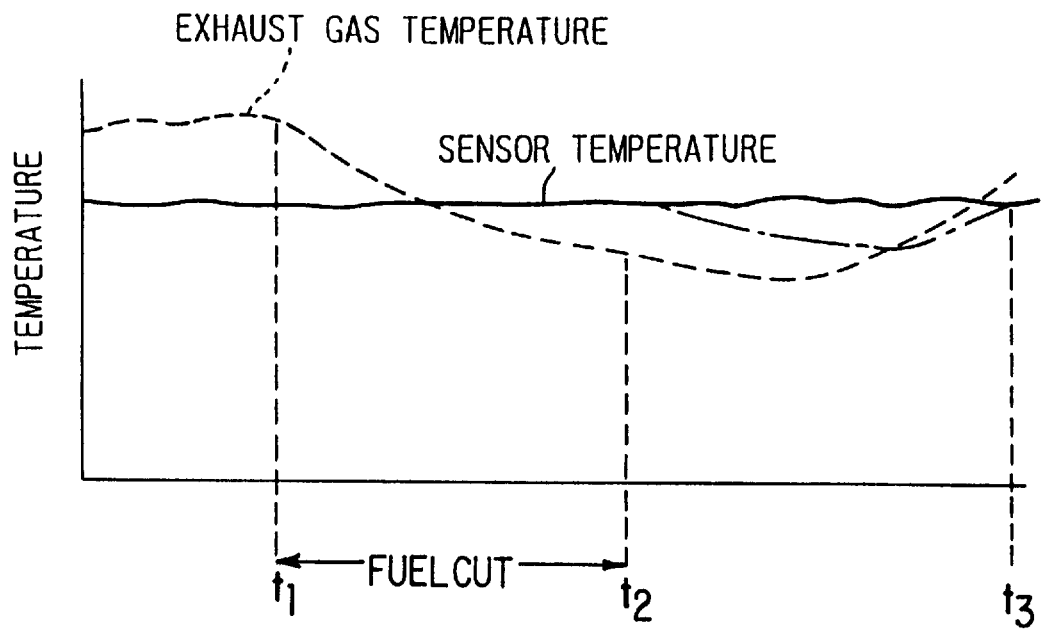
FIGS. 12A and 12B are graphs that show an effect of this invention.
Figure 12B:
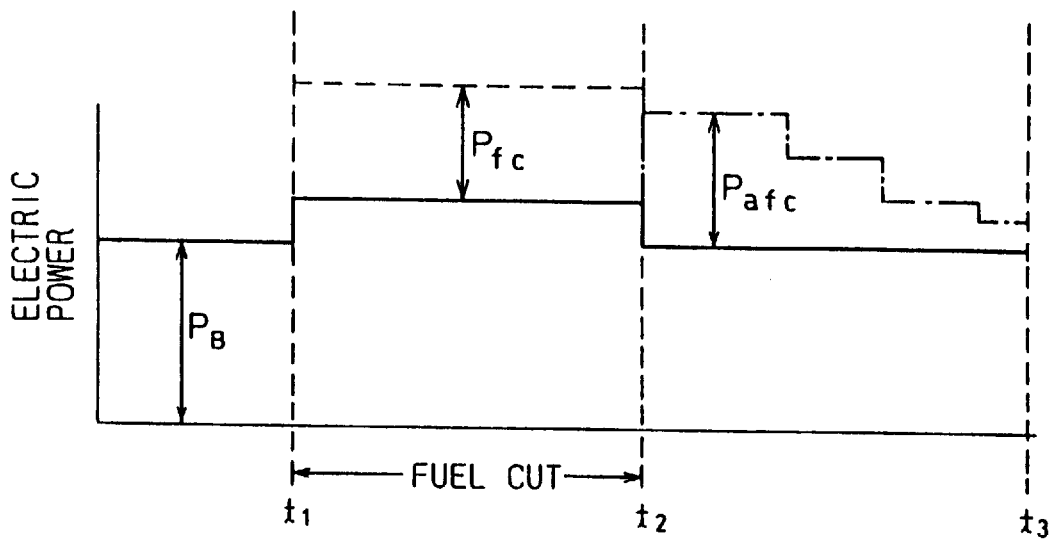

FIG. 12 is a graph to show an effect of the heater controller according to this invention. Ordinates of (a) and (b) denote respectively a temperature and an electric power, and abscissas of (a) and (b) denote time.

In (a), a solid line and a dashed line show respectively air-fuel ratio, and a dotted line shows the temperature of the exhaust gas.

In (b), a solid line shows the basic electric power Pb, a dotted line shows an auxiliary electric power Pfc during fuel-cut state, and a dashed line shows an auxiliary electric power Pafc after a return from a fuel-cut state.

Before a time $t_1$, the temperature of the air-fuel ratio sensor 11 is maintained at a predetermined proper temperature (for example, 650° C.) by the heater to which the basic electric power inherently determined by the engine operating condition is supplied.

When the fuel is cut at the time $t_1$, the temperature of the exhaust gas decreases because intake air is directly exhausted to the exhaust pipe 107 through the cylinder. During a fuel-cut state, it is possible to maintain the temperature of the sensor at the proper temperature because the electric power supplied to the heater is increased by the auxiliary electric power during fuel-cut state though the basic electric power is decreased as an intake vacuum Pm is nearly zero.

According to the prior art, a temperature fall in the sensor is not avoidable as shown the dashed line in (a), because the ambient temperature around the sensor is maintained at a low temperature though the basic electric power Pb returns to the level before the fuel-cut state.

On the other hand, according to this invention the temperature of the sensor can be maintained near the proper temperature between a time $t_2$ and $t_3$ as shown the solid line in (a), because an electric power is increased not only by the auxiliary electric power during the fuel-cut state but also by the auxiliary electric power after the return from the fuel-cut state.

I claim:

1. A heater controller for controlling electric power supplied to a heater for heating an air-fuel ratio sensor which detects an air-fuel ratio of an internal combustion engine, comprising:

an engine condition detecting means for detecting an operating condition of the internal combustion engine;

a basic electric power determining means for determining a basic electric power supplied for heating the sensor in accordance with the engine operating condition detected by said engine condition detecting means;

a fuel-cut state detecting means for detecting whether or not the engine is operating under a fuel-cut state;

an index calculating means for calculating an index which denotes a temperature fall in an atmosphere around the sensor when it is determined that the engine is operating under the fuel-cut state by said fuel-cut state detecting means;

an auxiliary electric power determining means for determining an auxiliary electric power in accordance with the index calculated by said index calculating means when it is determined that the engine has returned from the fuel-cut state by said fuel-cut state detecting means; and an electric power supplying means for supplying an electric power which is a sum of the basic electric power determined by said basic electric power determining means and the auxiliary electric power determined by said auxiliary electric power determining means.

2. The heater controller of claim 1, wherein said index calculating means uses an integral of an air flow rate during the fuel-cut state as the index.

3. The heater controller of claim 2, wherein said auxiliary electric power determining means determines an auxiliary electric power in accordance with the integrated air-flow rate during the fuel-cut state and an integral of an air-flow rate during a predetermined fixed interval after the return from the fuel-cut state.

4. The heater controller of claim 3, wherein said auxiliary electric power determining means determines an auxiliary electric power in accordance with a sum of a plurality of every integrated air-flow rate during the fuel-cut state which happens for a predetermined fixed term and a sum of a plurality of every corresponding integrated air-flow rate during a predetermined fixed interval after the fuel-cut state.

5. The heater controller of claim 1, wherein said index calculating means uses a temperature fall in the coolant during the fuel-cut state as the index.

6. The heater controller of claim 5, wherein said auxiliary electric power determining means determines an auxiliary electric power in accordance with the temperature fall in the coolant during the fuel-cut state and an integral of an air-flow rate during a predetermined fixed interval after the return from the fuel-cut state.

7. The heater controller of claim 6, wherein said auxiliary electric power determining means determines an auxiliary electric power in accordance with a sum of a plurality of every temperature fall in the coolant during the fuel-cut state which happens for a predetermined fixed term and a sum of a plurality of every corresponding integrated air-flow rate during a predetermined fixed interval after the fuel-cut state.

8. The heater controller of claim 1, wherein said index calculating means uses a temperature fall in the exhaust gas as the index.

9. The heater controller of claim 8, wherein said auxiliary electric power determining means determines an auxiliary electric power in accordance with the temperature fall in the exhaust gas during the fuel-cut state and an integral of an air-flow rate during a predetermined fixed interval after the return from the fuel-cut state.

10. The heater controller of claim 9, wherein said auxiliary electric power determining means determines an auxiliary electric power in accordance with a sum of a plurality of every temperature fall in the exhaust gas during the fuel-cut states which happens for a predetermined fixed term and a sum of a plurality of every corresponding integrated air-flow rate during a predetermined fixed after the fuel-cut states.

11. A heater control method for controlling an electric power supplied to a heater for heating an air-fuel ratio sensor which detects an air-fuel ratio of an internal combustion engine, comprising the steps of:

detecting an operating condition of the internal combustion engine;

determining a basic electric power supplied to the heater in accordance with the engine operating condition detected at said operating condition detecting step;

detecting whether or not the engine in fuel-cut state;

calculating an index which denotes a temperature fall in an atmosphere around the air-fuel ratio sensor when it is determined that the engine is in fuel-cut state at said fuel-cut state detecting step;

determining an auxiliary electric power in accordance with the index calculated at said index calculating step when it is determined that the engine returns from fuel-cut state at said fuel-cut state detecting step; and supplying an electric power which is a sum of the basic electric power determined at said basic electric power determining step and the auxiliary electric power determined at said auxiliary electric power determining step.

12. The heater control method of claim 11, wherein said index calculating step uses an integral of an air flow rate during the fuel-cut state as the index.

13. The heater control method of claim 12, wherein said auxiliary electric power determining step determines an auxiliary,electric power in accordance with the integrated air-flow rate during the fuel-cut state and an integral of an air-flow rate during a predetermined fixed interval after the return from the fuel-cut state.

14. The heater control method of claim 13, wherein said auxiliary electric power determining step determines an auxiliary electric power in accordance with a sum of a plurality of every integrated air-flow rate during the fuel-cut state which happens for a predetermined fixed term and a sum of a plurality of every corresponding integrated air-flow rate during a predetermined fixed interval after the fuel-cut state.

15. The heater control method of claim 11, wherein said index calculating step uses a temperature fall in the coolant during the fuel-cut state as the index.

16. The heater control method of claim 15, wherein said auxiliary electric power determining step determines an auxiliary electric power in accordance with the temperature fall in the coolant during the fuel-cut state and an integral of an air-flow rate during a predetermined fixed interval after the return from the fuel-cut state.

17. The heater control method of claim 16, wherein said auxiliary electric power determining step determines an auxiliary electric power in accordance with a sum of a plurality of every temperature fall in the coolant during the fuel-cut state which happens for a predetermined fixed term and a sum of a plurality of every corresponding integrated air-flow rate during a predetermined fixed interval after the fuel-cut state.

18. The heater control method of claim 11, wherein said index calculating step uses a temperature fall in the exhaust gas as the index.

19. The heater control method of claim 18, wherein said auxiliary electric power determining step determines an auxiliary electric power in accordance with the temperature fall in the exhaust gas during the fuel-cut state and an integral of an air-flow rate during a predetermined fixed interval after the return from the fuel-cut state.

20. The heater control method of claim 19, wherein said auxiliary electric power determining step determines an auxiliary electric power in accordance with a sum of a plurality of every temperature descent of the exhaust gas during the fuel-cut states which happens for a predetermined fixed term and a sum of a plurality of every corresponding integrated air-flow rate during a predetermined fixed after the fuel-cut states.

* * * * *